United States Patent [19]
Cooper et al.

[11] Patent Number: 5,836,988
[45] Date of Patent: Nov. 17, 1998

[54] RATE RESPONSIVE PACEMAKER WITH EXERCISE RECOVERY USING MINUTE VOLUME DETERMINATION

[75] Inventors: Daniel Cooper, Hauguenau, France; Tibor A. Nappholz, Englewood, Colo.; Chih-ming James Chiang, Chandler, Ariz.

[73] Assignee: Pacesetter, Inc., Sylmar, Calif.

[21] Appl. No.: 850,692

[22] Filed: May 2, 1997

[51] Int. Cl.⁶ ................................................. A61N 1/365
[52] U.S. Cl. ............................................. 607/19; 607/17
[58] Field of Search ........................................ 607/17–19

[56] References Cited

U.S. PATENT DOCUMENTS

| | | |
|---|---|---|
| 4,803,987 | 2/1989 | Calfee et al. . |
| 4,901,725 | 2/1990 | Nappholz et al. . |
| 5,081,988 | 1/1992 | Cook et al. . |
| 5,159,932 | 11/1992 | Zanetti et al. . |
| 5,387,229 | 2/1995 | Poore ........................................ 607/18 |
| 5,441,523 | 8/1995 | Nappholz . |
| 5,487,753 | 1/1996 | MacCarter et al. . |
| 5,562,711 | 10/1996 | Yerich et al. . |
| 5,562,712 | 10/1996 | Steinhaus et al. . |
| 5,609,613 | 3/1997 | Woodson et al. . |
| 5,626,662 | 5/1997 | Cooper ..................................... 607/18 |

*Primary Examiner*—William E. Kamm
*Assistant Examiner*—Carl H. Layno
*Attorney, Agent, or Firm*—Gottlieb, Rackamn & Reisman, P.C.

[57] ABSTRACT

A rate responsive implantable pacemaker generates a metabolic demand parameter which is converted into a corresponding metabolic indicated parameter. The parameter is used to determine certain characteristics related to an exercise period and the patient, including exercise duration and intensity. These characteristics are used to dynamically calculate an exercise recovery period during which the pacing rate is elevated above a rate indicated by the metabolic parameter. Preferably, fuzzy logic circuitry is used for this purpose.

18 Claims, 6 Drawing Sheets ary advantageous.
RATE RESPONSIVE PACEMAKER WITH EXERCISE RECOVERY USING MINUTE VOLUME DETERMINATION

RELATED APPLICATIONS

| | | |
|---|---|---|
| RATE-RESPONSIVE PACEMAKER WITH RAPID MINUTE VOLUNE DETERMINATION | 08/850,557 | 5/2/97 |
| RATE-RESPONSIVE PACEMAKER WITH NOISE-REJECTING MINUTE VOLUME DETERMINATION | 08/848,968 | 5/2/97 |
| RATE-RESPONSIVE PACEMAKER WITH MINUTE VOLUME DETERMINATION AND EMI PROTECTION | 08/850,529 | 5/2/97 |

BACKGROUND OF THE INVENTION

1. Field of the Invention

This invention relates to rate-responsive pacemakers and, more particularly, to pacemakers that employ a minute volume metabolic demand sensor as a metabolic rate indicator, said sensor operating appropriately to thereby insure that the pacemaker reacts accurately to changes in the level of activity, especially to recovery from short or long-term exercise.

2. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include physiological parameters such as the QT interval, respiration rate, venous oxygen saturation, stroke volume, venous blood temperature, and minute volume or ventilation, among others. (The terms minute ventilation and minute volume are used interchangeably). In addition, other metabolic demand parameters are also used based on physical activity as a criteria. More specifically, mechanical and electrical sensors are used to detect patient motion. Of the various parameters available, it has been found that pacemakers using minute volume as a parameter for controlling pacing rate are particul A problem with the current minute ventilation sensor is that for the recovery stage of patient exercise, no adjustment has been made for intensity of exercise, duration of exercise, which may cause unphysiological response. Publications in the field have identified these factors as important in affecting a fast or slow recovery from exercise.

No current minute ventilation sensor contains means to actively adjust for the recovery stage of exercise. A patent by Bonnet, et al., "Method and Apparatus for Controlling the Pacing Rate of a Metabolic Demand Pacemaker," (U.S. Pat. No. 5,249,572), contains a state space approach in which during recovery a low-pass filter with different time constant than during the onset is utilized to adjust for recovery from exercise. However, the time constant for the filter is programmable and there is no physiological basis which takes into consideration factors such as exercise duration, and exercise in the selection of the programmable time constant of the filter used in recovery of exercise.

Other prior art on fine-tuning paced rate during recovery from exercise include two patents, Bennett, et al., "Rate Responsive Pacemaker and Pacing Method" (U.S. Pat. No. 5,134,997), and Shelton, et al., "Rate Responsive Cardiac Pacemaker and Method for Work-Modulating Pacing Rate Deceleration," (U.S. Pat. No. 5,312,453). These prior patents were targeted for the activity-based sensor which did not respond well physiologically to the recovery phase of exercise, dropping almost immediately to the resting heart rate level at the cessation of exercise. Although these two patents incorporated the duration and intensity of exercise as criteria for recovery, the algorithms do not model physiologic observations in the most appropriate manner. As a result, the algorithms are contrived, complicated, and difficult to understand.

OBJECTIVES AND SUMMARY OF THE INVENTION

In view of the above mentioned disadvantages of the prior art, it is an objective of the present invention to provide a pacemaker which dynamically and physiologically responds to the recovery stage of patient exercise.

Another further objective is the utilization of fuzzy logic methodology to provide for the exercise recovery determination.

Other objectives and advantages of the invention shall become apparent from the following description. Briefly, a pacemaker constructed in accordance with this invention includes sensing means for sensing a metabolic demand parameter of the patient indicative of his or her instantaneous physical activity. Preferably, the metabolic demand parameter is minute volume which can be determined, for example, from impedance measurements. Minute volume has been found to be an accurate representation of the physical activity and the corresponding blood flow and oxygen demand of a patient. This parameter is converted into a corresponding metabolic indicated rate (MIR), which rate may be used to define the interval between the pacer pulses. The mapping of minute volume to metabolic indicated rate (MIR), preferably, uses a preselected curve which may be, for example, an exponential curve, or another type of monotonic curve. Next, an exercise recovery determination is applied to the curve to compensate for changes in the baseline due to exercise. The resulting rate is then used to calculate a optimal paced pulse interval.

DETAILED DESCRIPTION OF THE INVENTION

Figure 1:
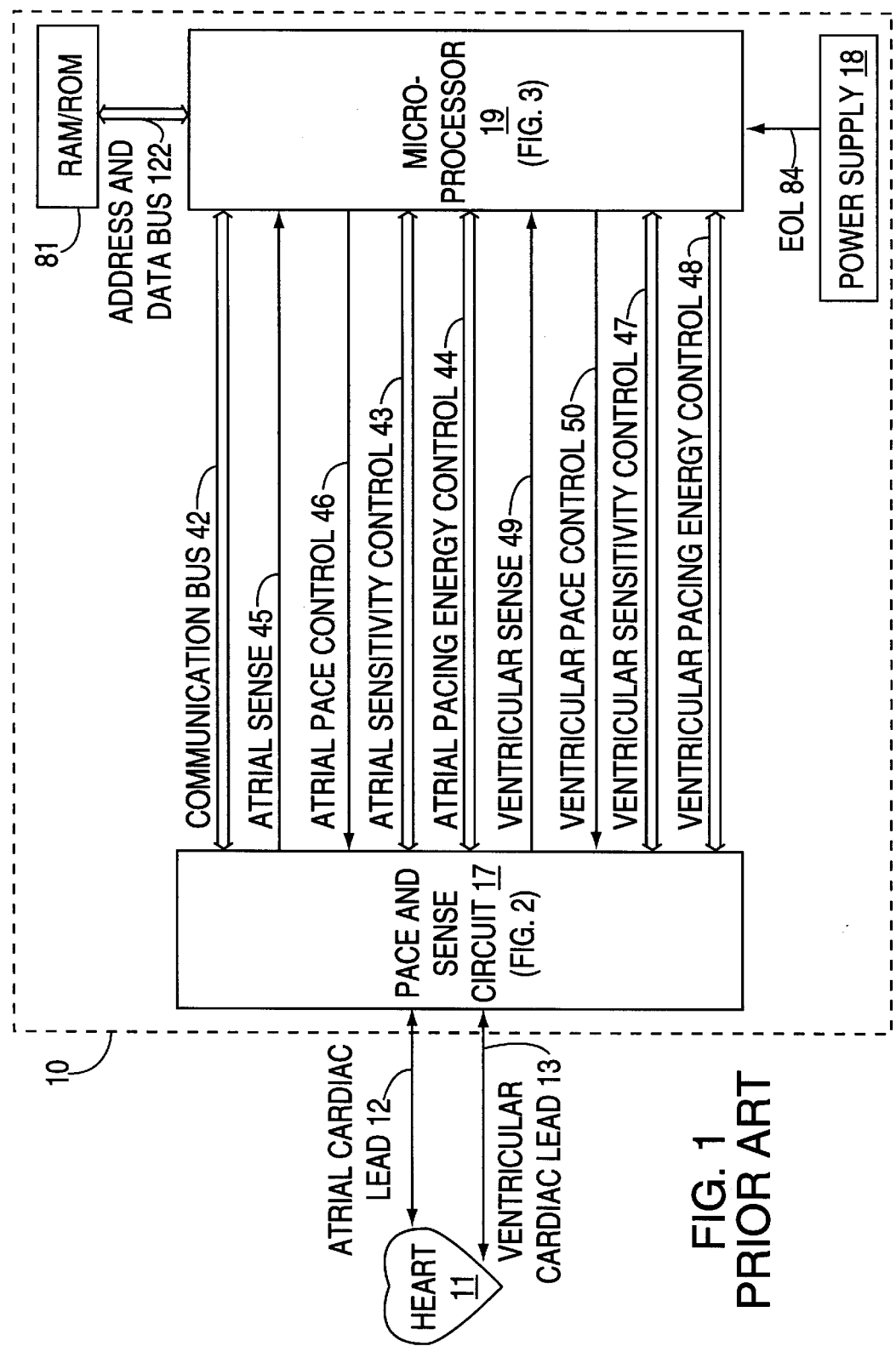
FIG. 1 shows a block diagram of a pacemaker constructed in accordance with this invention.

Details of a pacemaker in accordance with the present invention are shown in FIGS. 1–6. FIG. 1 shows a block diagram of the pacemaker. The pacemaker 10 is designed to be implanted in a patient and is connected by leads 12 and 13 to a patient's heart 11 for sensing and pacing the heart 11 as described for example in U.S. Pat. No. 5,441,523 by T. Nappholz, entitled FORCED ATRIOVENTRICULAR SYNCHRONY DUAL CHAMBER PACEMAKER, and incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 81 by an address and data bus 122. A low power signal line 84 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
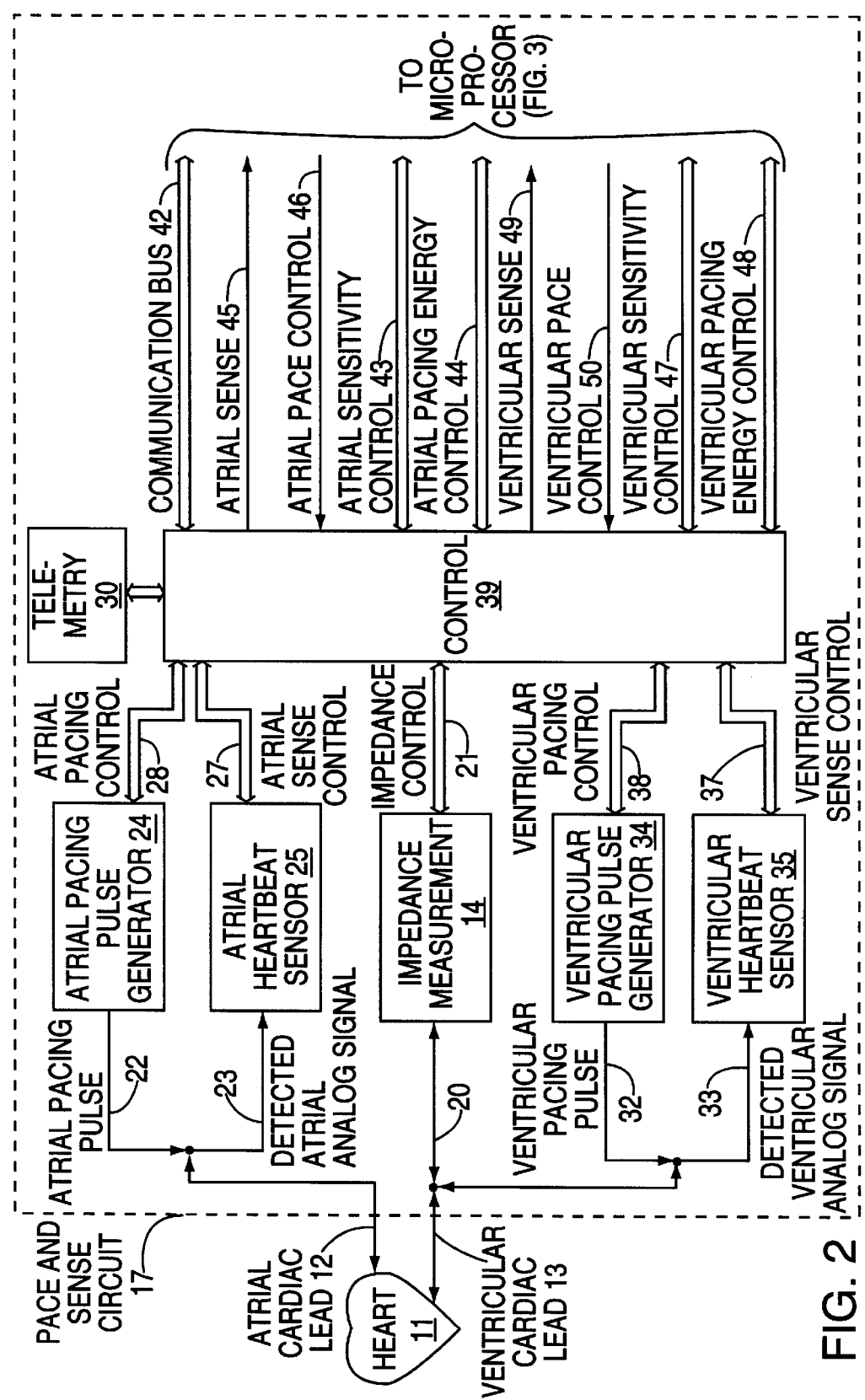
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that take place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current, as discussed in more detail below. These current and voltage signals define an impedance characteristic of the patient's metabolic demand, and more particularly, of the instantaneous minute volume. This instantaneous minute volume is then filtered and further modified by subtracting from it a long term average value, as discussed above. The resulting parameter is the minute volume parameter.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 3:
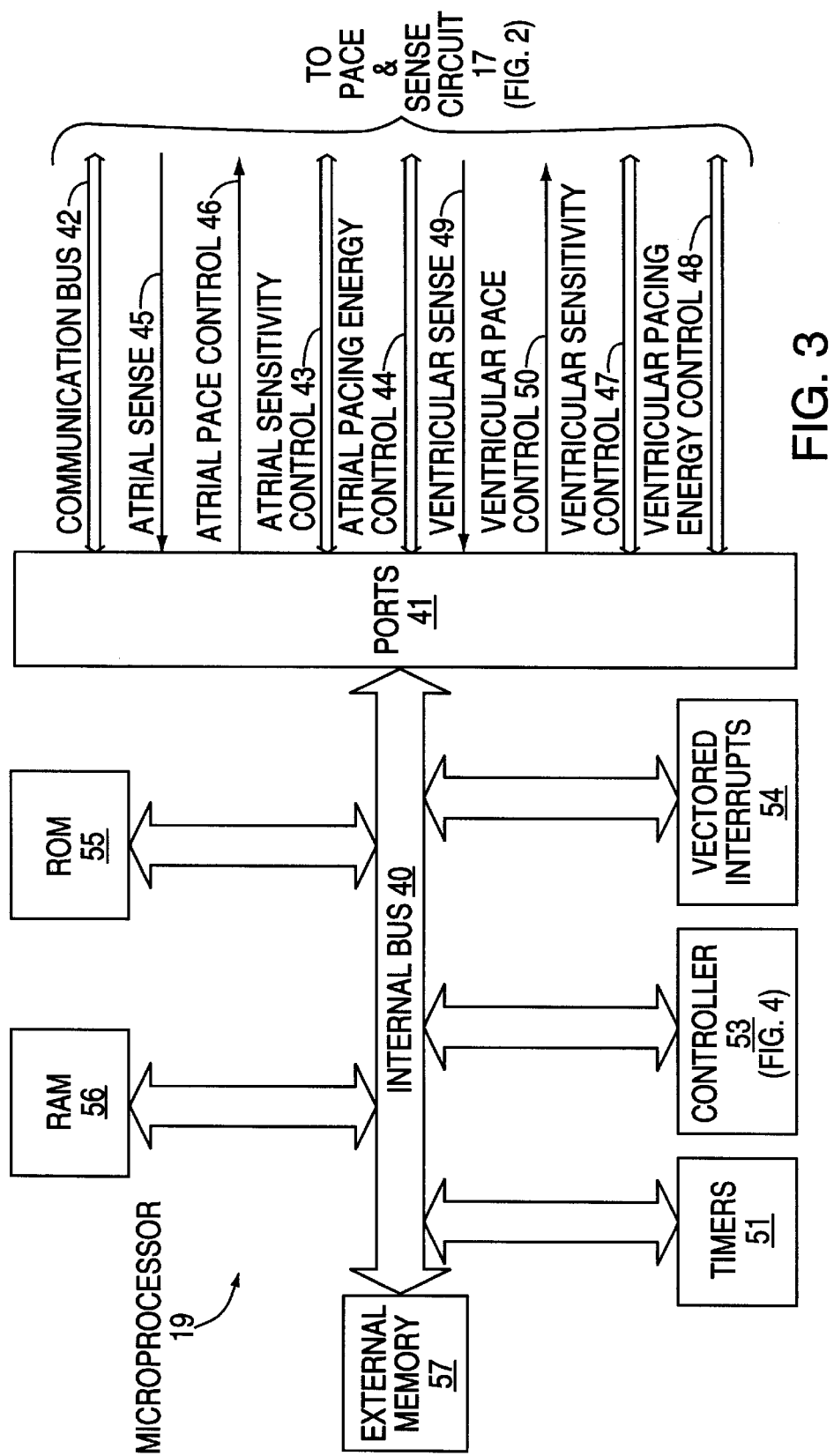
FIG. 3 shows a block diagram of a microprocessor for the pacemaker of FIG. 2.

FIG. 3 shows the microprocessor 19 having a timer circuit 51 for generating several timing signals, a controller 53, a vectored interrupts circuit 54, a ROM 55, a RAM 56, an external memory 57 and an interface port 41. Signals between these elements are exchanged via an internal communications bus 40. The RAM 56 acts as a scratch pad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data such as that concerning the functioning of the pulse generator 10 and the electrogram provided by the ventricular cardiac lead 13. The timer circuit 51, and its associated control software, implements some timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its ports 41 receives status and/or control inputs from the pace and sense circuit 17, including the sense signals on the sense lines 45 and 49 previously described. Using controller 53, it performs various operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricle pacing is adjusted by controller 53 as set forth below.

The pacemaker 10 of the present invention will function properly using any metabolic indicator rate system, so long as that system is able to reliably relate the sensed parameter to an appropriate matching of metabolic demand with the paced rate. However, the preferred embodiment of the invention employs the impedance measurement circuit 14, shown in FIG. 5, which measures the thoracic impedance to determine the respiratory minute volume as described generally in U.S. Pat. No. 4,901,725 to T. A. Nappholz, et al., issued Feb. 20, 1990 for "Minute Volume Rate-Responsive Pacemaker," incorporated herein by reference.

Figure 4:
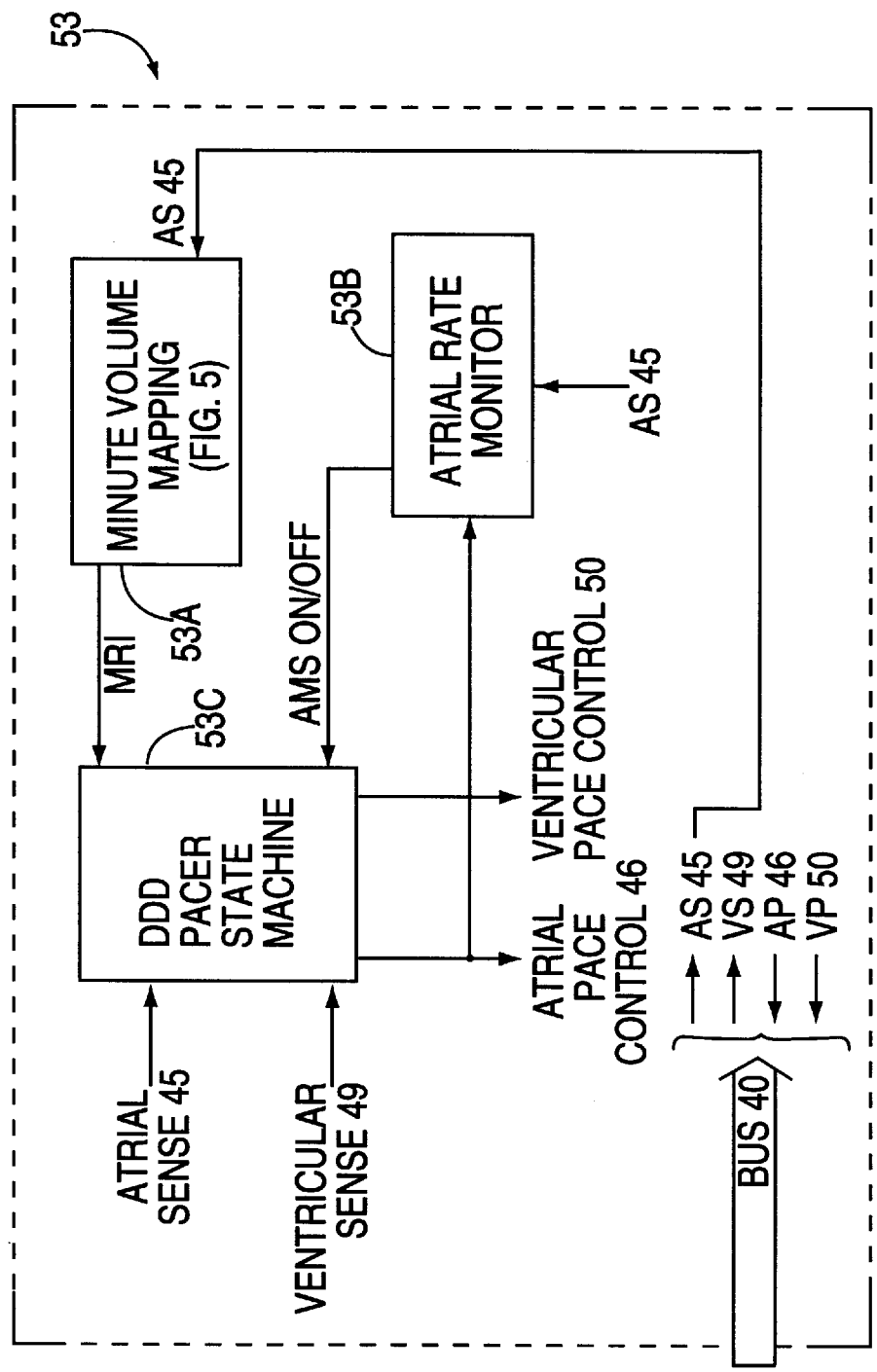
FIG. 4 shows details of the controller for the microprocessor of FIG. 3.

FIG. 4 shows the block diagram of the controller 53 of FIG. 3. The controller 53 includes a pacer 53C, which is preferably a state machine, a minute volume processor 53A and an atrial rate monitor 53B. The minute volume processor 53A uses the data supplied via the internal bus 40 and the communication bus 42 from the impedance measurement block 14 to relate the minute volume indicated by the impedance measurement to the Metabolic Rate Interval (MRI). This interval is then used by the pacer 53C to determine the length of each interval in the timing cycle. While the pacemaker 10 is preferably operating in a DDD mode, it should be understood that it can operate in other modes as well. The atrial rate monitor 53B generates an Automatic Mode Switching (AMS) signal upon detection of a non-physiological atrial rate and rhythm. This AMS signal automatically switches the pacemaker 10 to a pacing mode which is non-atrial tracking. When a physiological atrial rate resumes, the AMS signal is deactivated and the pacemaker returns to an atrial tracking mode.

Figure 5:
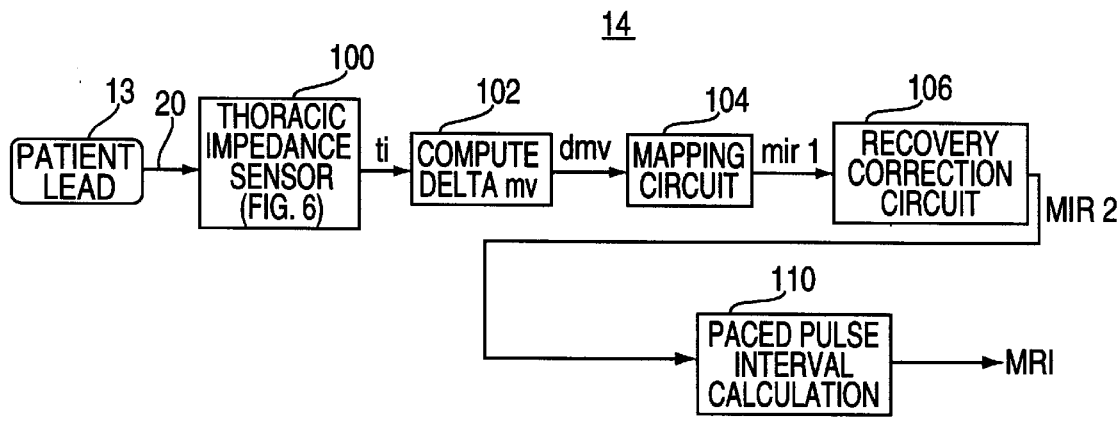
FIG. 5 shows details of the minute volume processor for the controller of FIG. 4.

Referring now to FIG. 5, impedance measurement circuit 14 includes a thoracic impedance sensor 100 which is coupled by connection 20 to one or both of the patient's leads, such as lead 13. The sensor 100 generates a time-dependent signal ti indicative of the sensed thoracic impedance of the patient. The signal ti is fed to a delta mv generator 102 which converts this ti signal into a corresponding dmv signal. The signal dmv is fed to a mapping circuit 104 which uses a conformal mapping (discussed in more detail below) to generate a corresponding metabolic indicated rate MIR1.

Signal MIR1 is fed to an exercise recovery correction circuit 106. The operation of circuit 106 is discussed more fully below in conjunction with FIG. 8. The correction circuit 106 generates a baseline corrected signal MIR2. This latter signal MIR2 is fed to the paced pulse interval calculator 110 to generate the metabolic rate interval (MRI).

Figure 6:
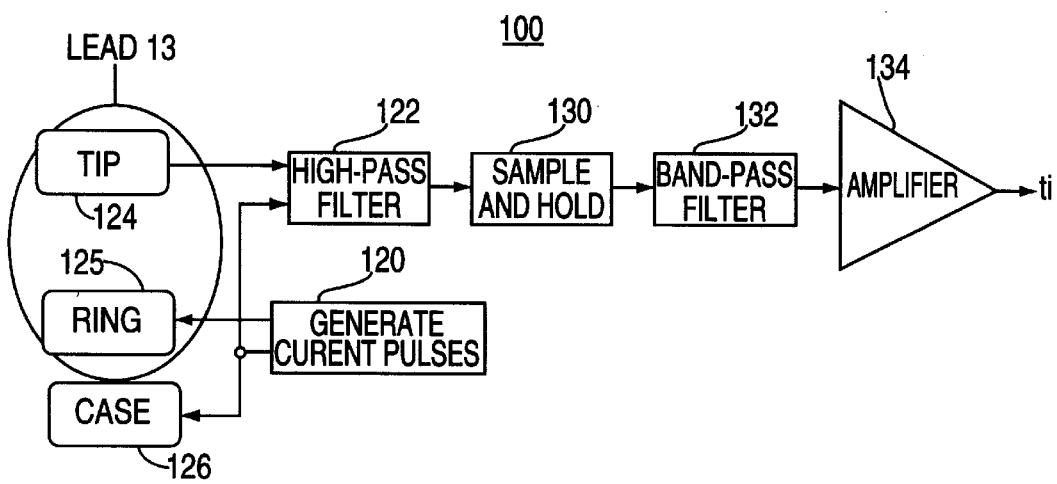
FIG. 6 shows a block diagram for the circuit used to determine thoracic impedance.

Referring now to FIG. 6, a known thoracic impedance sensor 100 includes a current generator 120 and a high pass filter 122 coupled to one of the patient leads, such as lead 13. (It should be emphasized that other leads may be used as well for determining the mv parameter as described for example in U.S. Pat. No. 5,562,712). The lead 13 includes a tip electrode 124 and a ring electrode 125. As known in the art, at predetermined times, the current generator 120 applies current pulses between the ring electrode 125 and pacemaker case 126, and the corresponding voltage is sensed between the tip electrode 124 and case 126. Typically, each current pulse has a pulse width of about 7.5 $\mu$sec, at repetition rate of about 18 pulses per second and an amplitude of about 1 mA. This pulse repetition rate is chosen at well above twice the Nyquist sampling rate for the highest expected intrinsic heart rate, and is preferably chosen so that it can be easily differentiable from noise induced by a power line at 50 or 60 Hz.

The sensed voltage is passed through the high pass filter 122 selected to accept the 7.5 $\mu$sec pulses and exclude noise signals. After filtering, the voltage signal is sampled by a sample and hold (S/H) circuit 130. Preferably, the S/H circuit takes samples before the start of the test pulses from generator 120 (to enhance the effectiveness of the filter 122) as well as toward the end of the pulse duration.

The output of circuit 130 is passed through a band pass filter 132 which selects the signals in the range of normal respiration rate, which is typically in the range of 5–60 cycles/minute.

The output of the BPF 132 is amplified by amplifier 134 to thereby generate the thoracic impedance signal ti. The amplifier raises the signal ti to a level sufficient so that it can be sensed and processed by the delta minute volume generator 102.

Circuit 102 is prior art and details can be found in U. S. Pat. No. 4,901,725 to T. A. Nappholz, et al., issued Feb. 20, 1990 for "Minute Volume Rate-Responsive Pacemaker," incorporated herein by reference.

The output from Circuit 102, the dmv value, must be converted into a metabolic indicated rate (MIR) parameter by mapping circuit 104. Schemes for performing this function are well known in the art. One such scheme is disclosed in copending application Ser. No. 08/641,223 filed Apr. 30, 1996, entitled RATE RESPONSIVE PACEMAKER WITH AUTOMATIC RATE RESPONSE FACTOR SELECTION incorporated herein by reference. As disclosed in this reference, a curvilinear mapping between minute ventilation and MIR is preferable because it can be modeled after physiological data on a wide range of normal subjects.

Figure 7:
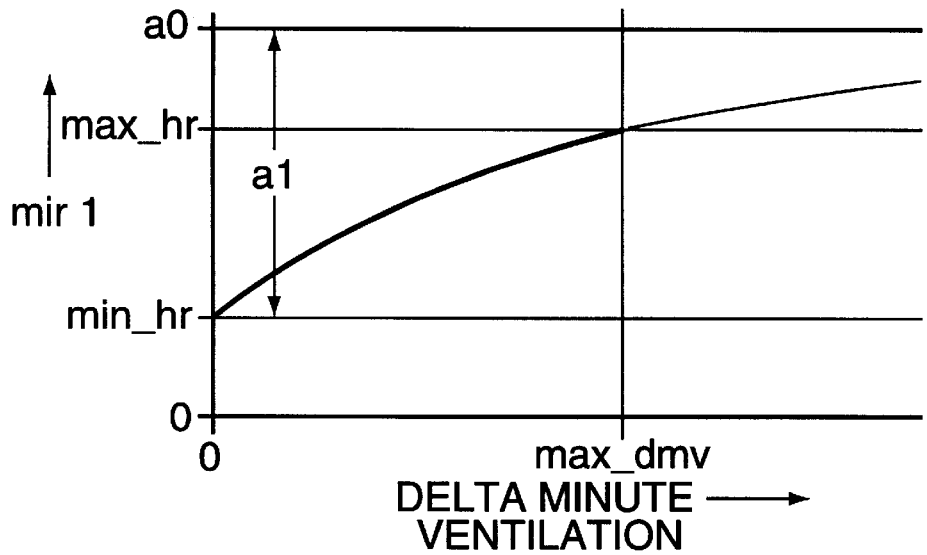
FIG. 7 shows an exponential mapping function mapping dmv in to MIR.

More particularly, it has been found that an excellent fit can be generated if an exponential mapping function is used. One such function is shown in FIG. 7. To save computational time, the exponential function may be performed by an interpolated table look-up function. The logarithmic function used to compute max_dmv is evaluated by the programmer, only at the time min_hr or max_hr is changed. The rate response factor (RRF) is defined so that one unit change in RRF relates to a 10% change in the peak value minute ventilation signal. It may be computed and displayed by the programmer, or may be entered by the user and used to initialize mv_gain.

The mapping function of FIG. 7 is defined by the following:

MIR1=a0−a1* exp(−dmv/a2)

a0=the upper heart rate asymptote, typically 230 pulses per minute a1=a0−min_hr (a1 determines min_hr)

a2=max_dmv/ln(a1/a0−max_hr) (a2 determines max_hr)

dmv=filtered delta minute ventilation from delta mv generator 102 max_dmv=the value of dmv which is mapped to max_hr max_hr=the programmed maximum value of paced heart rate RRF=rrf_const+ln (mv_gain/max_dmv)/ln (1.1)

mv_gain=max_dmv*1.1 (RRF−rrf_const)

rrf_const is chosen to establish the nominal RRF values at a preselected point along the curve of FIG. 7.

Next, the exercise recovery correction circuit 106 applies recovery correction to the signal MIR1 to model the observation that baseline heart rate is elevated following high level exercise. Circuit 106 is preferably implemented digitally as follows.

Figure 8A:
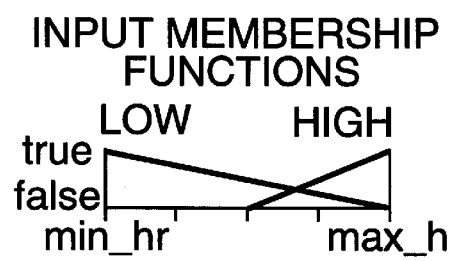
FIG. 8A shows the input membership functions for the exercise recovery circuit of FIG. 5.
Figure 8B:
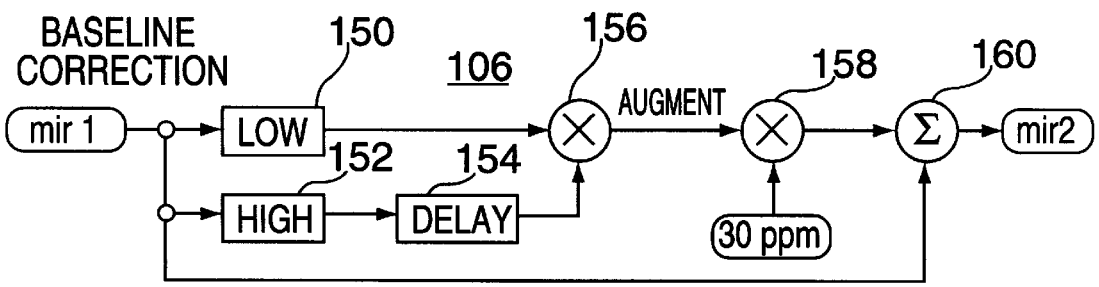
FIG. 8B shows a block diagram for the baseline correction circuit of FIG. 5.

The algorithm for the recovery correction circuit following exercise can be seen in FIGS. 8A and 8B. The metabolic indicated rate MIR1 is first inputted through the fuzzy input membership functions LOW 150 and HIGH 152 defined in FIG. 8A. The output from HIGH 152 is then entered into a Delay 154 whose function can be described below:

if (y>x) delay=delay+k1*(y−x)

if (y<x) delay=delay−k2*(x−y)

x=input y=output
k1=T/rise_time
k2=T/fall_time
rise_time=10 minutes
fall_time=40 minutes
T=iteration interval
delay=delay accumulator (initialized to zero)

Then the outputs from LOW 150 and HIGH 152 through Delay 154 are multiplied by multiplier 156 and multiplied by a second multiplier 158 with 30 pulses per minute (ppm) to derive the augmented rate. The output from multiplier 158 is then summed by summer 160 with the original MIR1 to result in the output MIR2 which is utilized to convert to pacing pulse intervals in calculator 110 (FIG. 5).

The rationale for this recovery algorithm is based upon the physiology that rate remains elevated following the cessation of exercise and that the rate of recovery is dependent upon exercise intensity, and exercise duration. From the Figures and the formulas, it can be seen that the rate augmentation occurs only when the present rate is low and the past rate has been high as in recovery from exercise. The delay function serves to elevate the present rate. The longer the delay function, the longer the overall heart rate remains elevated. The delay is a function of exercise duration, as indicated by the time constants k1 and k2. The delay is also a function of the exercise intensity, as indicated by the increase of the output of delay with heart rate increase (assuming that exercise intensity is a function of heart rate elevation).

Getting back to FIG. 5, the parameter MIR2 is then used to generate a metabolic indicated rate interval (MRI) by calculator 110. The paced pulse interval is inversely related to the paced heart rate as indicated by the following equation.

ppi=60000/phr where ppi=paced pulse interval, milliseconds phr=paced heart rate, pulses per second Other time intervals of the pacing cycle are computed by the state machine 53C (FIG. 4) using the paced pulse interval and/or the heart rate.

The subject invention has been described in the content of a rate-responsive pacemaker, using minute ventilation as the metabolic demand parameter. However, one skilled in the art will recognize that it is equally applicable to pacemakers using other metabolic demand parameters, including both the physiological and physical activity parameters discussed above.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A rate responsive implantable pacemaker for implantation in a patient, said pacemaker comprising:

a cardiac sensor for sensing cardiac activity and for generating a cardiac activity signal;

a pace generator for generating pacing pulses in response to pacing commands;

a parameter sensor for sensing a metabolic demand parameter;

a parameter processing circuit for processing said metabolic demand parameter to generate a metabolic indicated parameter;

an exercise recovery identifying circuit for identifying when said patient is recovering from exercise, said exercise recovery circuit generating a corresponding recovery signal;

a controller receiving said cardiac activity signal, said exercise recovery signal and said metabolic indicated parameter for generating said pacing commands.

2. The pacemaker of claim 1 wherein said controller includes an adjusting circuit that adjusts said pacing commands dependent on a duration of said exercise.

3. The pacemaker of claim 1 wherein said controller includes an adjusting circuit that adjusts said pacing commands dependent on metabolic indicated rate elevation duration during exercise.

4. The pacemaker of claim 1 wherein said controller includes an adjusting circuit that adjusts said pacing commands dependent on an intensity of said exercise.

5. A rate responsive implantable pacemaker for implantation in a patient, said pacemaker comprising:

a cardiac sensor for sensing cardiac activity and for generating a cardiac activity signal;

a pace generator for generating pacing pulses in response to pacing commands;

a parameter sensor for sensing a metabolic demand parameter;

a parameter processing circuit for processing said metabolic demand parameter to generate a metabolic indicated parameter;

an exercise sensor for sensing when said patient is performing an exercise having a duration and an intensity, said exercise sensor generating corresponding exercise signals identifying said duration and intensity of said exercise; and a controller receiving said cardiac activity signal, said exercise signals and said metabolic indicated parameter for generating said pacing commands.

6. The pacemaker of claim 5 wherein said controller includes an adjusting circuit that adjusts said pacing commands dependent on a duration of said exercise.

7. The pacemaker of claim 5 wherein said controller includes an adjusting circuit that adjusts said pacing commands dependent on metabolic indicated rate elevation duration during exercise.

8. The pacemaker of claim 5 wherein said controller includes an adjusting circuit that adjusts said pacing commands dependent on an intensity of said exercise.

9. A rate responsive implantable pacemaker for implantation in a patient, said pacemaker comprising:

a cardiac sensor for sensing cardiac activity and for generating a cardiac activity signal;

a pace generator for generating pacing pulses in response to pacing commands;

a parameter sensor for sensing a metabolic demand parameter;

a parameter processing circuit for processing said metabolic demand parameter to generate a metabolic indicated parameter;

an exercise sensor that senses when said patient is exercising and generates an end signal indicating that said patient has stopped exercising;

a delay circuit for generating a delayed parameter by delaying said metabolic demand parameter when said end signal is generated by said exercise sensor; and a controller receiving said cardiac activity signal and said delayed parameter for generating said pacing commands.

10. The pacemaker of claim 9 wherein said delay circuit is adapted to delay said metabolic indicated parameter by a delay period.

11. The pacemaker of claim 9 wherein said delay circuit is adapted to delay said metabolic indicated parameter by a function of exercise intensity.

12. The pacemaker of claim 9 wherein said delay circuit is adapted to delay said metabolic indicated parameter by a function of exercise duration.

13. The pacemaker of claim 9 wherein said delay circuit includes a fuzzy logic circuit.

14. The pacemaker of claim 13 wherein said fuzzy logic circuit includes a first element defining a high membership function for said metabolic indicated parameter and a delay element for delaying the output of said first element.

15. The pacemaker of claim 14 wherein said fuzzy logic circuit further comprises a second element defining a low membership function and a combiner element for combining the outputs of said second element and said delay element.

16. The pacemaker of claim 9 further comprising a condition sensor for sensing the physical condition of the patient from said metabolic indicated parameter, said delay circuit delaying said metabolic indicated parameter based on said condition.

17. The pacemaker of claim 16 wherein said condition sensor includes a fuzzy logic circuit having an input member defining an input membership function for said metabolic indicated parameter, and an output member defining an output membership function from said input member.

18. The pacemaker of claim 9 wherein said parameter sensor senses a minute volume.

* * * * *